United States Patent
Bobbert

(10) Patent No.: US 7,658,953 B2
(45) Date of Patent: Feb. 9, 2010

(54) ENHANCED ACTIVITY BIOCIDAL HYDROGEN PEROXIDE COMPOSITION

(75) Inventor: Ilja Bobbert, Loosdrecht (NL)

(73) Assignee: Aseptix Research B.V., Loenen aan de Vecht (NL)

( * ) Notice: Subject to any disclaimer, the term of this patent is extended or adjusted under 35 U.S.C. 154(b) by 432 days.

(21) Appl. No.: 11/331,136

(22) Filed: Jan. 13, 2006

(65) Prior Publication Data

US 2007/0166398 A1 Jul. 19, 2007

(51) Int. Cl.
  *A01N 39/00*   (2006.01)
  *A01N 37/00*   (2006.01)
  *A01N 57/26*   (2006.01)
  *A61K 9/00*    (2006.01)
  *C11D 3/395*   (2006.01)
  *C11D 3/00*    (2006.01)
  *C07F 9/09*    (2006.01)

(52) U.S. Cl. .................. 424/616; 424/400; 514/137; 514/557; 510/302; 510/347; 510/467

(58) Field of Classification Search .......... None
  See application file for complete search history.

(56) References Cited

U.S. PATENT DOCUMENTS

| 5,376,387 | A | * | 12/1994 | Monticello | .......... 424/616 |
| 6,444,230 | B1 | | 9/2002 | Godin et al. | |
| 6,479,454 | B1 | | 11/2002 | Smith et al. | |
| 6,518,307 | B2 | * | 2/2003 | McKenzie et al. | .......... 514/557 |
| 6,908,891 | B2 | | 6/2005 | Biering et al. | |

FOREIGN PATENT DOCUMENTS

| DE | 44 18 847 A1 | 12/1995 |
| FR | 2 751 634 A1 | 1/1998 |
| GB | 2 401 875 A | 11/2004 |
| WO | WO 97/25106 A1 | 7/1997 |
| WO | WO 97/31093 | 8/1997 |
| WO | WO 00/35289 | 6/2000 |
| WO | WO 01/65939 A1 | 9/2001 |
| WO | WO 03/067989 | 8/2003 |
| WO | WO 2004/067194 A2 | 8/2004 |
| WO | WO 2004/104147 * | 12/2004 |
| WO | WO 2006/076334 A1 | 7/2006 |

* cited by examiner

*Primary Examiner*—Johann R Richter
*Assistant Examiner*—Tigabu Kassa
(74) *Attorney, Agent, or Firm*—Oliff & Berridge, PLC

(57) ABSTRACT

The present invention discloses a biocidal composition comprising hydrogen peroxide in a concentration of 0.05-50% (w/w) and a compound with a structure according to Formula 1:

(OH)(X)(O)P—O—(CH—(Y)—CH$_2$—O)$_n$—R, or a salt thereof, wherein X is H or OH, Y is H or CH$_3$, n is 2-6 and R is an alkyl radical containing 4-18 carbon atoms, in a concentration of 0.01-60% (w/w). A especially preferred compound according to Formula 1 is a compound wherein X is OH, Y is H, n is 4 and R is a straight alkyl chain containing 10 carbon atoms.

19 Claims, No Drawings

ENHANCED ACTIVITY BIOCIDAL HYDROGEN PEROXIDE COMPOSITION

The present invention relates to the field of disinfection and cleaning, more specifically to enhanced biocidal activity compositions based on hydrogen peroxide that also possess enhanced stability.

Numerous classes of chemical compounds exhibit varying degrees of biocidal or antimicrobial activity. Biocidal compositions are needed, among other things, to clean and disinfect food surfaces such as fruits and vegetables and to clean and disinfect hard-surfaces in the health care industry, food and beverage industries and household area.

In the past few years, efforts have been concentrated on developing chemicals that will be highly effective against microorganisms when in a diluted form, will be low in toxicity to humans and other animals, and will not be harmful to the environment.

Of the known disinfectants and biocidals, hydrogen peroxide appears to have exceptional potential, because the decomposition products, water and oxygen, are not toxic and not harmful to the environment. Also, it tends to have a broad spectrum biocidal activity. Broad spectrum activity is important for instance in situations where harmful organisms are present but their identity is not known. Hydrogen peroxide-based disinfectants are useful in many different applications, including in hospitals, clinics, laboratories, dental offices, home care and chronic care facilities. They may also be used in food and beverage processing and preparation, animal husbandry, the hospitality industry and for general sanitation.

In order to provide fast, effective action, biocidal hydrogen peroxide solutions had to employ relatively high concentrations of hydrogen peroxide. However, at higher concentrations, the solutions may be subject to hazardous goods regulations and may require special precautions for handling and use. For example, at concentrations of above about 8 w/w % aqueous solution, hydrogen peroxide is considered corrosive and is also a strong oxidizing agent. Solutions containing less than about 8 w/w % hydrogen peroxide are preferred for their improved safety profile.

Compositions based on hydrogen peroxide as the only biocidal compound and containing up to 7% hydrogen peroxide by weight of the total composition are not fully efficacious to disinfect soiled surfaces, e.g., surfaces which needs both to be washed and disinfected. Indeed, the presence of organic and/or inorganic soils decreases the bactericidal activity of many antimicrobials like peroxygen-based agents, resulting thereby in a lower bactericidal activity and disinfection power of compositions comprising them.

At low concentrations (e.g. 3% w/w), hydrogen peroxide is non-irritating to skin, but exhibits low germicidal activity. For example, a solution containing 3% w/w hydrogen peroxide takes 20 minutes to achieve a greater than 6 log reduction in Staphylococcus aureus, which is too long for many applications. Increasing the concentration of hydrogen peroxide will increase the rate of disinfection. For example, a 25% w/w aqueous solution of hydrogen peroxide requires only 20 seconds to achieve a greater than 6 log reduction in Staphylococcus aureus. However, the solution is corrosive at this concentration and requires special handling procedures.

Another drawback of the use of hydrogen peroxide compositions is that without the use of a stabiliser, or a combination of stabilisers, the aqueous peroxide compositions characteristically may decompose over a relatively short time period.

Several solutions are proposed in the art to obtain hydrogen peroxide compositions with enhanced biocidal activity.

WO 97/31093 discloses a disinfecting composition comprising a peroxygen bleach, e.g. hydrogen peroxide, an amphoteric surfactant, e.g. betaine, glutaraldehyde and an antimicrobial essential oil.

WO 01/65939 discloses bactericidal properties of a combination of hydrogen peroxide, a benzalkonium salt and an inorganic phosphate sequestering agent.

U.S. Pat. No. 6,479,454 and U.S. Pat. No. 6,444,230 disclose improved antimicrobial activity of the combination of a peroxygen compound with an amine oxide.

WO 03/067989 discloses the use of certain anionic sulfonic acid-based surfactants in combination with hydrogen peroxide.

It is an object of the present invention to provide compositions which deliver excellent biocidal activity using as low as possible hydrogen peroxide concentrations and/or as less as possible further biocidal additives. Also, an objective has been to provide a composition that can be applied without handling or usage precautions, safety measures, and that does not require rinsing or only scarce rinsing after application. It is surprisingly shown by the present invention that compositions comprising a combination of hydrogen peroxide with certain phosphate or phosphonate compounds show an enhanced biocidal activity. The compositions also exhibit a significant increase in stability as compared to hydrogen peroxide solutions not containing the compound in question.

Thus, in a first aspect, the present invention provides a composition comprising hydrogen peroxide in a concentration of 0.05-50% (w/w) and a compound with a structure according to Formula 1:

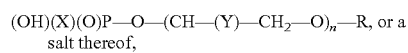

wherein X is H or OH, Y is H or $CH_3$, n is 2-6 and R is an alkyl radical containing 4-18 carbon atoms, in a concentration of 0.01-60% (w/w).

Such a composition surprisingly has an excellent biocidal activity, even upon dilution to a composition comprising 0.05-8% of hydrogen peroxide and 0.01-10% of a compound with a structure according to Formula 1. It also displays a good stability over time. The combination of hydrogen peroxide and the compound according formula 1 provides a more potent biocide than that can be obtained by using these two compounds separately.

Unless indicated otherwise, percentages used throughout this invention are weight percentages based on the total weight of the composition.

The compound with a structure according to Formula 1 comprises a polar head group and a long, hydrophobic carbon tail also containing hydrophilic oxygen atoms. It is found to be advantageous that this tail comprises a linear backbone chain comprising at least 14, preferably at least 16, carbon atoms, extending from the phosphorous. These at least 14 carbon atoms may be provided by the alkoxy (ethylene or propylene oxide) groups as well as the alkyl group.

In a preferred structure according to Formula 1, X is OH, Y is H, n is 4-6, preferably 4, and/or R is an alkyl radical containing 4-16 carbon atoms, preferably 6-14 carbon atoms, more preferably 8-12 carbon atoms, even more preferably 10 carbon atoms. Most preferably, R is a straight chain alkyl radical.

An especially preferred compound according to the invention is a compound with a structure according to Formula 1 wherein X is OH, Y is H, n is 4 and R is a straight chain alkyl radical containing 8-12 carbon atoms, preferably 10 carbon atoms.

It will be apparent to the skilled person that heterogeneous compounds, wherein the value for n and/or the length of the alkyl radical are variable, with the value for n and the chain length as specified above being average values, are also encompassed in the present invention.

The composition of the invention preferably may be sold as a concentrate comprising hydrogen peroxide in a concentration that may range from about 10-50% and the compound with a structure according to Formula 1 in a concentration that may range from about 5-60%. Said concentrate may suitably be diluted to the effective concentration to be used in the final application.

Upon dilution, the effective hydrogen peroxide concentration of the composition of the invention may be 0.05-8% (w/w), preferably 0.1-5%, more preferably 0.2-3%, most preferably 0.3-2%. Depending on the intended use of the composition of the invention, the hydrogen peroxide concentration may be in the higher range, e.g. from 1-8%, or in the lower range, e.g. from 0.05-1%. The concentration of the compound with a structure according to Formula 1 may be 0.01-10% (w/w), preferably 0.05-5%, more preferably 0.1-2%.

The concentration of hydrogen peroxide and the compound with a structure according to Formula 1 in the composition of the invention preferably is chosen in such a way that the weight ratio between hydrogen peroxide and the compound with a structure according to Formula 1 varies between 10 and 0.1, more preferably between 5 and 0.2, most preferably between 2 and 0.5.

Due to the effectiveness of the combination of hydrogen peroxide and the compound with a structure according to Formula 1, the composition of the invention may be used as a formulation which is as simple as possible. For many applications it may not be necessary to supplement the composition of the invention with additional compounds influencing (enhancing) its biocidal activity. Thus, in such embodiments, the composition of the invention consists essentially of hydrogen peroxide and the compound with a structure according to Formula 1 as compounds with biocidal activity.

Biocidal activity of a composition of the invention is determined by a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements).

The biocidal peroxide composition of the invention preferably is an aqueous solution.

In a preferred embodiment, the biocidal peroxide composition of the invention is a ready-to-use aqueous solution comprising 0.1-5% hydrogen peroxide and 0.05-5% of a compound with a structure according to Formula 1, such as Monafax® 1214 (Uniqema). The pH of the solution preferably is 2-5.

Such composition also is very ecologically friendly. Monafax 1214 is a highly biodegradable product and has received ecolabelling from the Swedish Society for Nature Conservation. This enables the use of the solution in situations where environmentally friendly products are preferred.

Various other compounds may be added to the composition of the invention to enhance its practical utility.

For instance, a pH adjusting acid (organic or inorganic) or base or an appropriate buffer may suitably be added to provide the composition of the invention with a pH of choice.

Preferably, the composition of the invention has a pH in the acidic region, more preferably a pH of 1-8, even more preferably a pH of 1.5-6, and most preferably a pH of 2-5.

The composition of the invention further may comprise a hydrogen peroxide stabilizer, preferably in the form of a cation sequestering agent, more preferably in a concentration of 0.01 to 20% (w/w). The cation sequestering agent may be chosen from ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), and salts thereof or from benzoic acid, aminobenzoic acid, citric acid, phosphoric acid, iminodisuccinic acid and polyaspartic acid. More preferably, the cation sequestering agent is a (colloidal) stannate, and even more preferably is chosen from acetanilide, trisodium ethylenediamine disuccinate, for instance OctaQuest E30 or A65 (Octel), phosphonic acid derivatives having 1 to 5 phosphonic acid groups, for instance a Dequest phosphonate (Solutia), 1-hydroxyethylidene-1,1-diphosphonic acid, amino tri(methylene phosphonic acid), diethylenetriamine-penta(methylene phosphonic acid), 2-hydroxy ethylimino bis(methylene phosphonic acid), and ethylene diamine tetra(methylene phosphonic acid).

The composition of the invention further may comprise a corrosion inhibitor, preferably, in a concentration of 0.01% to 20% w/w. Preferably, the corrosion inhibitor is chosen from 1,2,3 benzotriazole, sodium molybdate, sodium nitrite, sodium bisulfate, sodiummetabisulfate, chromates, borates, phosphates, polyphosphates, sodium benzoate, sodium gluconate and sodium silicate.

The composition may also comprise a hydrogen peroxide compatible surfactant. This surfactant may be an anionic, a cationic, a nonionic and/or an amphoteric surfactant, preferably a nonionic and/or an anionic surfactant. The surfactant concentration may be from 0.005 to 40% w/w.

Exemplary hydrogen peroxide compatible nonionic surfactants are ethoxylated alcohols and alkylglycosides having a hydrophile lyophile balance from 5 to 15 and/or sufficiently water-soluble block copolymers of ethylene oxide or propylene oxide, a C6-C14 alkyl, 3-6 moles of ethylene oxide (EO) alcohol ethoxylate, or a combination thereof.

Exemplary hydrogen peroxide compatible anionic surfactants are alkyl sulfates, e.g. C8-C16 alkyl sulfates, alkyl ether sulfates, alkyl benzene sulfonic acids, e.g. alkali metal, alkaline earth metal, ammonium or alkylamine salts of C8-C16 alkyl benzene sulfonic acids, alkyl sulfonic acids, e.g. C8-C18 alkyl sulfonic acids, alkyl diphenyl oxide sulfonic acids, C6-C12 alkyl diphenyl sulfonates, naphthalene sulfonic acids, alkyl or alkenyl esters or diesters of sulfosuccinic acids, and salts thereof.

As well, the composition may comprise at least one C1 to C8 alcohol, preferably in a concentration of about 0.01 to about 10% w/w. The alcohol may be chosen from benzyl alcohol, ethanol, n-butanol, isopropanol and glycols, such as ethylene glycol, propylene glycol and butylene glycol.

Other additives may be added to the biocidal peroxide composition of the invention in order to provide the composition with properties suitable for its use. Examples of such additives are emulsifiers, hydrotropes, glycerol, fragrances, coloring chemicals, preservatives, anti-foam and corrosion inhibitors.

In another aspect, the present invention relates to the use of the biocidal hydrogen peroxide composition of the invention for any purpose where disinfecting and/or sanitizing and/or cleaning and/or bleaching and/or preservative activity is required, including, but not limited to, use as a bactericidal and sterilization liquid, and as cleaning, disinfection and sanitization agent.

In particular, the biocidal peroxide composition of the invention may be used for those applications where it is important to obtain disinfecting and/or sanitizing and/or cleaning and/or bleaching and/or preservative activity with the mildest agents possible, for instance domestic use, medical use, personal care, mouth care, food, clean rooms, etc. Also for applications where no or scarce rinsing after application is preferred, or where the solution may come into contact with food.

Since the biocidal peroxide composition of the invention is non-irritating, has no odors or volatile gasses, and is skin friendly, it is also optimal for situations where users do not wear any protective clothing, in cases where worker-safety has high priority or for personal application like wound disinfection or prevention of gingivitis.

The present invention also relates to the use of the biocidal peroxide composition in specific devices such as spray devices, e.g. spray bottles, aerosol cans, aerosol generation devices for room disinfection, and by application in the form of dipping.

A preferred use of the biocidal hydrogen peroxide composition of the present invention relates to the use as skin disinfecting agent, preferably for hand disinfection.

In order to enhance the practical utility and effectiveness as skin disinfectant, various skin-conditioning agents may be added to the composition of the invention. The skin-conditioning agent may be chosen from glycerides, sorbitol, castor oil, (water soluble) silicons, allantoin, cationic polymers, lanolin and its derivatives and cetyl alcohol.

The composition may further comprise nonionic surfactants to improve wetting capacity and enhance drying of the hands. Also fat, oil and/or stain removers and degreasers, such as anionic, nonionic or amphoteric surfactants or alcohols, may be added for specific situations where fat and stain removal is required.

A problem with existing skin disinfection products, typically containing alcohols, iodines/iodophors, chlorhexidine gluconate (CHG), phenolic compounds, quaternary ammonium compounds or combinations thereof, is that they often sacrifice disinfectant activity for the sake of skin mildness or vice versa. For example, while raising the concentration of the active ingredient may lead to a higher level of disinfection, such higher concentration frequently leads to increased skin irritation.

The skin (hand) disinfectant compositions of the invention may advantageously replace such disinfectants that have been developed to achieve high levels of disinfection where such need exists.

The composition of the invention is able to provide adequate levels of disinfection while not being irritating to the skin. The composition is non-irritating due to the low levels of hydrogen peroxide, mild surfactant package and low concentrations of other mild additives which may be employed as described above. The solution has broad-spectrum activity, the degree of which is unexpected given the germicidal activity of the individual ingredients. A synergy exists amongst the ingredients of the present inventive solution such that an effective disinfectant is provided that is suitable for use on skin.

Another preferred use of the composition of the invention relates to the use in dentistry and as mouth rinse. Infection and inflammation control in the mouth and oral cavities is still an important area and until today dominated by chlorine-, alcohol- and phenol-based products. Many of these products have significant drawbacks and have a negative influence on living tissue. The compositions of the present invention can effectively replace such products.

In order to have an effective composition for dentistry and mouth rinse, various compounds may be added to the composition of the invention to enhance its anti-microbial efficacy, such as anti-microbial essential oils and zinc salts, i.e. zinc chloride, zinc oxide, zinc lactate, or compounds that enhance the practical utility such as glycols, alcohols, edible surfactants, flavors, fragrances, etc.

The present invention further relates to the use of the composition of the invention for disinfecting and/or cleaning a substrate. This can be done by contacting the substrate with an effective amount of the biocidal composition of the invention. The composition is especially effective in the removal of stains and dirt. The substrate may be any surface, space, material, medical instrument or device, hospital equipment, surface of walls, ceilings and/or floors, preferably a substrate wherein the presence of (pathogenic) micro-organisms is suspected.

The composition of the invention further may be effectively used for food preservation, as rinsing liquid for meat, poultry and fish, as rinsing liquid in breweries and dairy production, for veterinary and cattle applications, such as prevention and treatment of mastitis, and for water treatment and water disinfection.

EXAMPLES

Biocidal activity of the exemplified compositions was tested using a controlled bactericidal suspension test conform European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements). One ml of a test suspension containing about $10^8$ cfu of the test microorganism per ml is added to 8 ml of the composition to be tested, and 1 ml milli-Q water is added. After 1, 2 and 5 minutes contact time, the amount of viable bacteria was determined.

Biocidal activity of some compositions was tested using a bactericidal suspension test conform European Norm EN 12054 for chemical disinfectants and antiseptics, in particular products for hygienic and surgical handscrub and handwash. One ml of a test suspension containing at least $1\times10^8$ cfu per ml bacteria is mixed with 9 ml of the composition to be tested. Firstly, the starting suspension is counted by diluting to countable levels. For the handrub test undiluted test suspensions are used. For the handwash test a hard water diluent is used.

Example 1

Various compositions were tested for biocidal activity and compared to standard, commercially available $H_2O_2$ solutions without any additions except for the stabilizers. The compositions of the invention tested included an aliphatic phosphate ester with 10 carbon atoms and 4 moles of ethyleneoxide (EO), for example such as sold by Uniqema International under the tradename Monafax 1214. Also a hydrogen peroxide stabilizer was present in the form of Trisodium Ethylenediamine Disuccinate, available from Octel under the tradename OctaQuest (OQ). The pH of such solution ranges between 2 and 4.5. The test results are presented in Table 1 below. It appears that the addition of Monafax significantly enhances biocidal activity of the composition.

TABLE 1

|  | test suspension | 1 min | 2 min | 5 min |
|---|---|---|---|---|
| 1.0% $H_2O_2$ + 0.02% OQ | | | | |
| Salmonella typhimurium | 4.80E+08 | >1000 | >1000 | >1000 |
| Escherichia coli | 6.00E+07 | >1000 | >1000 | 1000 |
| Pseudomonas aeruginosa | 1.25E+08 | >1000 | >1000 | 172 |
| Staphylococcus aureus | 5.35E+08 | >1000 | >1000 | 560 |
| Enterobacter cloacae | 7.50E+08 | >1000 | >1000 | >1000 |
| 1.5% $H_2O_2$ + 0.02% OQ | | | | |
| Salmonella typhimurium | 4.80E+08 | >1000 | >1000 | 1000 |
| Escherichia coli | 6.00E+07 | >1000 | 1000 | 688 |
| Pseudomonas aeruginosa | 1.25E+08 | 46 | 13 | 0 |
| Staphylococcus aureus | 5.35E+08 | >1000 | 1000 | 678 |
| Enterobacter cloacae | 7.50E+08 | >1000 | >1000 | 864 |
| 1.75% $H_2O_2$ + 0.02% OQ | | | | |
| Salmonella typhimurium | 4.80E+08 | >1000 | >1000 | >1000 |
| Escherichia coli | 6.00E+07 | >1000 | >1000 | 408 |
| Pseudomonas aeruginosa | 1.25E+08 | 670 | 210 | 48 |
| Staphylococcus aureus | 5.35E+08 | >1000 | 876 | 272 |
| Enterobacter cloacae | 7.50E+08 | >1000 | >1000 | 1000 |
| 2% $H_2O_2$ + 0.02% OQ | | | | |
| Salmonella typhimurium | 4.80E+08 | >1000 | >1000 | 1000 |
| Escherichia coli | 6.00E+07 | >1000 | 1000 | 576 |
| Pseudomonas aeruginosa | 1.25E+08 | 1000 | 650 | 2 |
| Staphylococcus aureus | 5.35E+08 | >1000 | 528 | 192 |
| Enterobacter cloacae | 7.50E+08 | >1000 | 1000 | 1000 |
| 0.6% $H_2O_2$ + 0.7% Monafax 1214 + 0.02% OQ | | | | |
| Salmonella typhimurium | 4.80E+08 | 0 | | |
| Escherichia coli | 6.00E+07 | 0 | | |
| Pseudomonas aeruginosa | 1.25E+08 | 0 | | |
| Staphylococcus aureus | 5.35E+08 | 0 | | |
| Enterobacter cloacae | 7.50E+08 | 0 | | |
| 1.0% $H_2O_2$ + 1% Monafax 1214 + 0.02% OQ | | | | |
| Salmonella typhimurium | 4.80E+08 | 0 | | |
| Escherichia coli | 6.00E+07 | 0 | | |
| Pseudomonas aeruginosa | 1.25E+08 | 0 | | |
| Staphylococcus aureus | 5.35E+08 | 0 | | |
| Enterobacter cloacae | 7.50E+08 | 0 | | |
| 1.0% $H_2O_2$ + 0.5% Monafax 1214 + 0.02% OQ | | | | |
| Salmonella typhimurium | 4.80E+08 | 0 | | |
| Escherichia coli | 6.00E+07 | 0 | | |
| Pseudomonas aeruginosa | 1.25E+08 | 0 | | |
| Staphylococcus aureus | 5.35E+08 | 0 | | |
| Enterobacter cloacae | 7.50E+08 | 0 | | |
| 1.5% $H_2O_2$ + 0.1% Monafax 1214 + 0.02% OQ | | | | |
| Salmonella typhimurium | 1.00E+08 | 0 | | |
| Escherichia coli | 4.00E+07 | 0 | | |
| Staphylococcus aureus | 1.35E+08 | 0 | | |
| Enterobacter cloacae | 1.15E+08 | 0 | | |
| 0.5% $H_2O_2$ + 0.2% Monafax 1214 + 0.02% OQ | | | | |
| Salmonella Typhimurium | 1.00E+08 | 0 | | |
| Escheria Coli | 4.00E+07 | 0 | | |
| Staphylococcus Aureus | 1.35E+08 | 0 | | |
| Enterobacter Cloacae | 1.15E+08 | 0 | | |
| 0.5% $H_2O_2$ + 0.5% Monafax 1214 + 0.02% OQ | | | | |
| Salmonella Typhimurium | 1.00E+08 | 0 | | |
| Escheria Coli | 4.00E+07 | 0 | | |
| Staphylococcus Aureus | 1.35E+08 | 0 | | |
| Enterobacter Cloacae | 1.15E+08 | 0 | | |

Without Monafax, only a few bacteria types show greater than log 5 reduction within 5 minutes, which is the test norm according standard EN 1276. With Monafax, a log 6 or even log 7 reduction is reached after already 1 minute.

Example 2

The performance of Monafax 1214 was compared with that of two widely used nonionic surfactants, the ethoxylated fatty alcohol Dehydol LT7 (C12-18 with 7 EO; Cognis) in 0.6% and Arlasolve 200 of Uniqema, a high HLB nonionic surfactant (polyoxyethylene isohexadecylether) in 0.7%, and a pH of around 5 using the EN 1276 test. The test results are presented in Table 2 below. It appears that the biocidal activity of compositions containing Monafax is significantly better than that of compositions containing the ethoxylated fatty alcohol or the high HLB nonionic surfactant.

TABLE 2

|  | test suspension | 1 min | 2 min | 5 min |
|---|---|---|---|---|
| 1.5% $H_2O_2$ + 0.1% Monafax 1214 + 0.02% OQ | | | | |
| Escherichia coli | 4.00E+07 | 0 | | |
| Staphylococcus aureus | 1.35E+08 | 0 | | |
| 1.5% $H_2O_2$ + 0.6% Dehydol LT7 + 0.02% OQ | | | | |
| Escherichia coli | 1.30E+08 | >500 | 96 | 12 |
| Staphylococcus aureus | 1.74E+09 | 220 | 196 | 60 |
| 1.5% $H_2O_2$ + 0.7% Arlasolve 200 + 0.02% OQ | | | | |
| Escherichia coli | 1.30E+08 | >500 | >500 | 48 |
| Staphylococcus aureus | 1.74E+09 | 304 | 204 | 72 |

Example 3

The performance of the solutions of the invention was compared to that of amine oxides, a group of surfactants known from the prior art (for example: U.S. Pat. No. 6,479,454 (Ecolab) and U.S. Pat. No. 6,444,230 (Chemoxal) to possess significant biocidal activity in a hydrogen peroxide solution, even at lower concentration ranges.

To simulate unclean practical conditions, a protein load was added according to the EN 1276 procedures to bacterial test suspensions. To provide for a clean condition 0.3% Bovine Albumin was added and for a dirty condition 3% Bovine Albumin. The performance of Monafax 1214 was compared with that of the N,N-Dimethyldecylamine-N-oxide (Barlox 10s of Lonza Ltd.). A $H_2O_2$ concentration of 1.2% was used and a 0.6% of the respective surfactants. The solution containing Monafax has a pH of around 2.3 and the solution containing Barlox 10s has a pH of around 5. The test results are presented in Table 3 below. It appears that the biocidal activity of compositions containing Monafax is significantly.

TABLE 3

|  | test suspension | clean 2 min | clean 5 min | dirty 2 min | dirty 5 min |
|---|---|---|---|---|---|
| Barlox 10s (Lonza) | | | | | |
| Enterococcus hirae | 3.80E+08 | 8 | 0 | 6 | 1 |
| Bacillus cereus | 2.20E+08 | >300 | >300 | >300 | >300 |
| Candida albicans | 3.00E+08 | 300 | 250 | >300 | >300 |
| Staphylococcus aureus | 5.50E+08 | >300 | >300 | >300 | >300 |
| Lysteria monocytogenes | 3.00E+08 | >300 | >300 | >300 | >300 |

TABLE 3-continued

| | test | clean | | dirty | |
|---|---|---|---|---|---|
| | suspension | 2 min | 5 min | 2 min | 5 min |
| Monafax 1214 (Uniqema) | | | | | |
| Lysteria monocytogenes | 3.00E+08 | 3 | 0 | 0 | 0 |
| Enterococcus hirae | 2.00E+08 | 0 | 0 | 0 | 0 |
| Escherichia coli | 3.00E+08 | 0 | 0 | 0 | 0 |
| Pseudomonas aeruginosa | 1.00E+08 | 0 | 0 | 0 | 0 |
| Staphylococcus aureus | 5.50E+08 | 0 | 0 | 0 | 0 |
| Enterobacter cloacae | 3.00E+08 | 0 | 0 | 0 | 0 |

>300 indicates a number of colonies that cannot be counted (overgrown)

Example 4

It also appears that the solutions of the invention are significantly more stable than solutions only containing hydrogen peroxide and commercially available hydrogen peroxide stabilizers. The stability of a 0.6% hydrogen peroxide solution in the presence of commercially available stabilizers was tested. Test settings were 37° C. for 30 days. The test results are presented in Table 4 below. The $H_2O_2$ concentration was measured with potassium permanganate titration. The blank contains only $H_2O_2$ with a stabilizer as added by the manufacturer (Solvay Chemicals).

The addition of Monafax 1214 enhances the stability of the hydrogen peroxide solution, even in the presence of commercially available hydrogen peroxide stabilizers.

TABLE 4

| 30 days at 37° C. | Octaquest 0.02% | Acetanilide 0.05% | Dequest 0.20% | Blank |
|---|---|---|---|---|
| without Monafax 1214 | −6.1% | −2.3% | −13.2% | −3.4% |
| with Monafax 1214 | −1.0% | 0.0% | 0.0% | −0.4% |

Example 5

A solution containing 0.5% hydrogen peroxide, 0.5% aliphatic phosphate ester (Monafax 1214 of Uniqema International), 0.5% Acetanilide as hydrogen peroxide stabilizer and 0.6% C10 alcohol ethoxylate (8 moles EO) (Lutensol XL 80 by BASF) and Potassium Hydroxide till pH 4.5 was prepared and used as hand disinfection scrub agent.

| | |
|---|---|
| Hydrogen Peroxide | 0.5% |
| Monafax 1214 (Uniqema) | 0.5% |
| Lutensol XL 80 (BASF) | 0.6% |
| Acetanilide | 0.5% |
| Potassium Hydroxide | to pH 4.5 |
| Demineralised Water | up to 100% |

The solution was tested for its antimicrobial activity using EN 12054 test method at *S. aureus, P. aeruginosa, E. hirae,* and *E. coli* and showed more than log 3 reduction which is the norm for a hand antiseptic.

The invention claimed is:

1. A composition comprising hydrogen peroxide in a concentration of 0.05-50% (w/w) and a compound with a structure according to Formula 1:

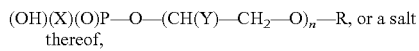

(OH)(X)(O)P—O—(CH(Y)—CH$_2$—O)$_n$—R, or a salt thereof, wherein X is H or OH, Y is H or CH$_3$, n is 2-6 and R is an alkyl radical containing 4-12 carbon atoms, in a concentration of 0.01-60% (w/w).

2. The composition of claim 1, wherein X is OH and Y is H.

3. The composition of claim 1, wherein X is OH, Y is H, n is 4, and R is an alkyl radical containing 8-12 carbon atoms.

4. The composition of claim 1, wherein R is a straight chain alkyl radical.

5. The composition of claim 1, wherein the hydrogen peroxide concentration is 0.05-8% (w/w).

6. The composition of claim 1, wherein the concentration of the compound with a structure according to Formula 1 is 0.01-10% (w/w).

7. The composition of claim 1, wherein the concentration of hydrogen peroxide and the compound with a structure according to Formula 1 is chosen in such a way that the weight ratio between hydrogen peroxide and the compound with a structure according to Formula 1 varies between 10 and 0.1.

8. The composition of claim 1, wherein the pH has a value of 1-8.

9. The composition of claim 1 further comprising a hydrogen peroxide stabilizer.

10. The composition of claim 1 further comprising a non-ionic and/or an anionic surfactant.

11. The composition of claim 1 further comprising a corrosion inhibitor.

12. A method of providing at least one activity selected from the group consisting of disinfecting, sanitizing, cleaning, bleaching and preservation, comprising applying the composition of claim 1 where such activity is required.

13. A method for disinfecting a substrate comprising:
applying an effective amount of the composition of claim 1 to a substrate, wherein a biocidal activity of the composition has at least a log 6 reduction of bacteria in a bacterial suspension containing about 1×10$^8$ cfu per ml of bacteria in at least one minute, when 9 ml of the composition is added to 1 ml of the bacterial suspension.

14. The method according to claim 13, wherein the at least one activity is disinfecting and cleaning the substrate.

15. The composition of claim 1, wherein a biocidal activity of the composition has at least a log 6 reduction of bacteria in a bacterial suspension containing about 1×10$^8$ cfu per ml of bacteria in at least one minute, when 9 ml of the composition is added to 1 ml of the bacterial suspension.

16. The composition of claim 1, wherein R is an alkyl radical containing 6-12 carbon atoms.

17. The composition of claim 1, wherein R is an alkyl radical containing 8-12 carbon atoms.

18. The composition of claim 1, wherein R is an alkyl radical containing 6-10 carbon atoms.

19. The composition of claim 1, wherein R is an alkyl radical containing 8-10 carbon atoms.

* * * * *

UNITED STATES PATENT AND TRADEMARK OFFICE
CERTIFICATE OF CORRECTION

| | | |
|---|---|---|
| PATENT NO. | : 7,658,953 B2 | Page 1 of 1 |
| APPLICATION NO. | : 11/331136 | |
| DATED | : February 9, 2010 | |
| INVENTOR(S) | : Ilja Bobbert | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 704 days.

Signed and Sealed this

Fourth Day of January, 2011

David J. Kappos
*Director of the United States Patent and Trademark Office*